(12) United States Patent
Kiraly et al.

(10) Patent No.: US 8,423,124 B2
(45) Date of Patent: Apr. 16, 2013

(54) METHOD AND SYSTEM FOR SPINE VISUALIZATION IN 3D MEDICAL IMAGES

(75) Inventors: Atilla Peter Kiraly, Plainsboro, NJ (US); Christopher V. Alvino, Allenwood, NJ (US); Hong Shen, Plainsboro, NJ (US)

(73) Assignee: Siemens Aktiengesellschaft, Munich (DE)

( * ) Notice: Subject to any disclaimer, the term of this patent is extended or adjusted under 35 U.S.C. 154(b) by 1091 days.

(21) Appl. No.: 12/150,663

(22) Filed: Apr. 30, 2008

(65) Prior Publication Data

US 2008/0287796 A1 Nov. 20, 2008

Related U.S. Application Data

(60) Provisional application No. 60/938,727, filed on May 18, 2007.

(51) Int. Cl.
*A61B 5/05* (2006.01)

(52) U.S. Cl.
USPC .......................................... 600/425; 600/443

(58) Field of Classification Search .................. None
See application file for complete search history.

(56) References Cited

U.S. PATENT DOCUMENTS

| | | | |
|---|---|---|---|
| 6,023,495 A | 2/2000 | Adler et al. | |
| 6,028,907 A | 2/2000 | Adler et al. | |
| 6,608,916 B1 | 8/2003 | Wei et al. | |
| 6,850,635 B2 | 2/2005 | Gerard et al. | |
| 6,978,039 B2 * | 12/2005 | Cline et al. | 382/128 |
| 7,095,881 B2 * | 8/2006 | Lelong et al. | 382/132 |
| 2005/0018885 A1 | 1/2005 | Chen et al. | |
| 2005/0117787 A1 * | 6/2005 | Iordanescu et al. | 382/128 |
| 2006/0110017 A1 * | 5/2006 | Tsai et al. | 382/128 |
| 2006/0173271 A1 * | 8/2006 | Shen et al. | 600/407 |
| 2007/0055178 A1 | 3/2007 | Verre et al. | |
| 2007/0092121 A1 | 4/2007 | Periaswamy et al. | |
| 2007/0121778 A1 | 5/2007 | Shen et al. | |
| 2007/0127799 A1 | 6/2007 | Reisman et al. | |

OTHER PUBLICATIONS

Bitter et al., Comparison of Four Freely Available Frameworks for Image Processing and Visualization That Use ITK, published online Jan. 10, 2007, IEEE Transactions on Visualization and Computer Graphics, vol. 13, No. 3, pp. 483-493.*

Yao et al., Automated Spinal Column Extraction and Partitioning, 2006, ISBI, p. 390-393.*

Archip et al., A Knowledge-Based Approach to Automatic Detection of the Spinal Cord in CT Images, 2002, IEEE Transactions on Medical Imaging, vol. 21, No. 12, pp. 1504-1516.*

Enders et al., Visualization of White Matter Tracts with Wrapped Streamlines, 2005, IEEE Visualization 2005, Oct. 23-28, Minneapolis, MN, USA, p. 51-58.*

Lell et al., New Techniques in CT Angiography, 2006, Clinical Applications of Vascular Imaging, RSNA, V 26, S45-S62.*

(Continued)

*Primary Examiner* — Long V. Le
*Assistant Examiner* — Bo J Peng (57) ABSTRACT

A method and system for visualizing the spine in 3D medical images is disclosed. A spinal cord centerline is automatically determined in a 3D medical image volume, such as a CT volume. A reformatted image volume is then generated based on the spinal cord centerline. The reformatted image volume can be a straightened spine volume or a Multi-planar Reconstruction (MPR) based volume that follows the natural curve of the spine. The reconstructed volume can be displayed as 2D slices or 3D volume renderings.

23 Claims, 7 Drawing Sheets

OTHER PUBLICATIONS

Kanitsar et al., CPR—Curved Planar Reformation, 2002, IEEE Visualization, Oct. 27-Nov. 1, 2002, Boston, MA, USA, p. 37-44.*

Vrotvec et al. (Automated curved planar reformation of 3D spine images, 2005, Phys. Med. Biol. 50, 4527-4540.*

Vrtovec, T., et al., "Curved Planar Reformation of CT Spine Data", SPIE Medical Imaging, p. 1446-1456, 2005. Proc. of SPIE, vol. 5747.

* cited by examiner

METHOD AND SYSTEM FOR SPINE VISUALIZATION IN 3D MEDICAL IMAGES

This application claims the benefit of U.S. Provisional Application No. 60/938,727, filed May 18, 2007, the disclosure of which is herein incorporated by reference.

BACKGROUND OF THE INVENTION

The present invention relates spine visualization in 3D medical images, and more particularly to reformatting 3D medical images for improved visualization of the spine.

3D medical images, or volumetric medical data, such as computed tomography (CT) images, typically contain a wealth of anatomical information. For example, a chest CT image taken to evaluate a patient's airways may also contain valuable information concerning the patient's spine. In order to view the spine in such CT image, the volumetric data can be analyzed using standard two 2D slices. However, using standard 2D slices to analyze spine information in the volumetric data is a tedious task, and it can be hard to see curvature and abnormalities of the spine since the spine passes through slices at an angle. It is possible to use volume rendering to view the volumetric data in 3D, but it is difficult to obtain an unobstructed view of the spine using standard volume rendering techniques because other anatomic structures, such as the ribs, block the view of the spine.

An approach to simple evaluation of the spine was presented in Vrtovec, et. al., "Curved planar reformation of CT spine data," SPIE Medical Imaging, pg. 1446-1456. 2005. In this process, a curved multiplanar image was obtained from the data via a spinal centerline. The centerline was computed by fitting a polynomial to a distance transform that is determined from a thresholded version of the image. The disadvantages of this method include the computational expense required from creating a distance function in the entire volume, a lack of robustness due to the specific choice of threshold, a high potential for overfitting due to the allowance of very high degree polynomials, and a lack of validation on the method itself with only one dataset tested. The method is not fully automatic and requires user input in order to complete, limiting its use for clinical applications. Finally, the method does not guarantee smooth transitions within the determined contour, limiting its utility in visualization.

BRIEF SUMMARY OF THE INVENTION

The present invention provides a fully automatic method and system for visualizing the spine in 3D medical images. Embodiments of the present invention generate improved views of the spine that can be used for further analysis or segmentation of the spine.

In one embodiment of the present invention, an input 3D image volume is received, and a spinal cord centerline is automatically determined in the 3D medical volume. The spinal cord centerline can de defined by a series of points that represent the position of the spinal cord in the input 3D image. A reformatted image volume is then generated from the input 3D volume based on the spinal cord centerline. The reformatted volume can be a straightened spine reformatted image volume or a Multi-planar Reconstruction (MPR) based reformatted image volume. The reformatted image volume can then be displayed by displaying 2D image slices of the reformatted image volume or 3D volume renderings of the reformatted image volume.

These and other advantages of the invention will be apparent to those of ordinary skill in the art by reference to the following detailed description and the accompanying drawings.

DETAILED DESCRIPTION OF EXEMPLARY EMBODIMENTS

The present invention is directed to a method for visualizing the spine in 3D medical images. Embodiments of the present invention are described herein to give a visual understanding of the spine visualization method. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system. For example, according to various embodiments of the present invention, electronic data representing a 3D medical image is manipulated within a computer system in order to reformat the image to visualize the spine.

Figure 1:
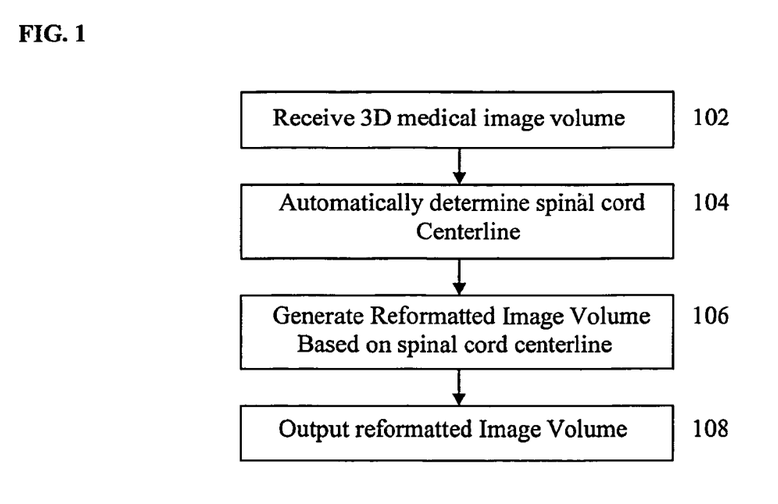
FIG. 1 illustrates a method for visualizing the spine in a 3D medical image volume according to an embodiment of the present invention.

FIG. 1 illustrates a method for visualizing the spine in 3D medical images according to an embodiment of the present invention. At step 102, a 3D medical image volume is received. The image volume is a 3D medical image of a portion of a patient's body. The image volume can be received from an image acquisition device that is used to scan the patient. For example, the image volume can be a 3D chest computed tomography (CT) image received from a CT scanner. The image volume can also be received by inputting or loading a volume that was previously acquired and stored, for example on storage or memory of a computer system. Although embodiments of the present invention are described using a CT volume, the present invention is not limited thereto, and any 3D medical image can be used, such 3D MRI data or 3D ultrasound.

At step 104, a spinal cord centerline is automatically determined in the 3D medical image volume by tracking the spinal cord. The spinal cord centerline is line detected in the image volume that estimates the location of the spinal cord through the center of the vertebrae in the spine. In order to determine the spinal cord centerline, an initial point can be determined inside the spinal cord of thoracic vertebrae in axial slices of the 3D image volume. The spinal cord appears as a dark circle in such axial slices. An annulus model can then be used which exhaustively determines an optimal position for a point in each successive axial slice, as well as inner and outer radii for maximizing a contrast score that uses the average image data inside the inner radius and subtracts it from the average image data between the inner radius and outer radius. The center of the annulus with the highest score in considered to lie at the center of the spinal cord, and thus the series of these points in the axial slices define the centerline. This spinal cord detection method is described in greater detail in U.S. patent application Ser. No. 11/539,273, filed on Oct. 6, 2006, which is incorporated herein by reference. The smoothness of the centerline from one axial slice to the next can be maintained by fitting a line through the previous K points, including the point in the current slice. This line is fit by finding the optimal line in three dimensions that minimizes the sum of the distances to each of these K points. According to a possible implementation, K=5 can be use, which yields an adequately smooth centerline, but this may vary depending on the axial resolution of the image volume.

The automated spinal cord centerline determination results in a series of N points $P_o \in [p_1 \ldots p_N]$, where each point is a 3D location in the image volume, and each point can be assigned a set of orthogonal direction vectors $(\vec{v}_d, \vec{v}_h, \vec{v}_w)$, which are described in greater detail below. Although the series of points may be adequate to delineate the spine, the transitions between the points may not be smooth enough to provide a good visualization. Once the points defining the centerline are determined, the points can be further smoothed, for example by performing cubic Hermite splines on a subset of points. For example, points every 6 mm on the original image volume can be used for interpolation. The spline is used to apply a new set of equidistant points. It can be noted that many original points are ignored in this smoothing process. However, this does not greatly affect the visualization. Any other method to ensure smoothness in transitions along with equidistant points can be similarly applied. The distance between the new points can be the minimum voxel size of the original image volume in order to generate a new image of approximately the same voxel dimensions, or can be set to a smaller amount to generate a super-sampled, i.e., magnified, image. This processing results in a new set of points, $P_r \in [p_1 \ldots p_M]$, that define the centerline, and are directly used to reformat the image volume in order visualize the spine. It is important to note that without any smoothness constraint, the final visualization can have artifacts and appear distorted.

Figure 5:
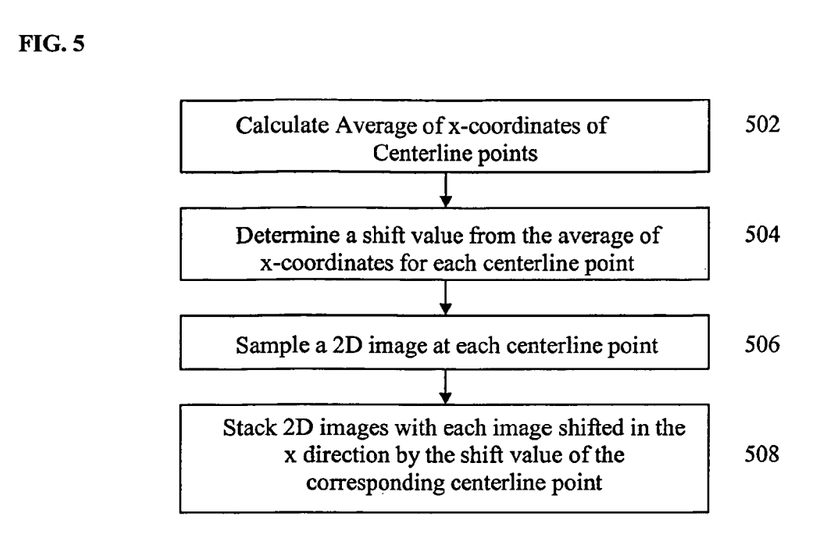
FIG. 5 illustrates a method for generating a reformatted image volume according to another embodiment of the present invention.
Figure 6:
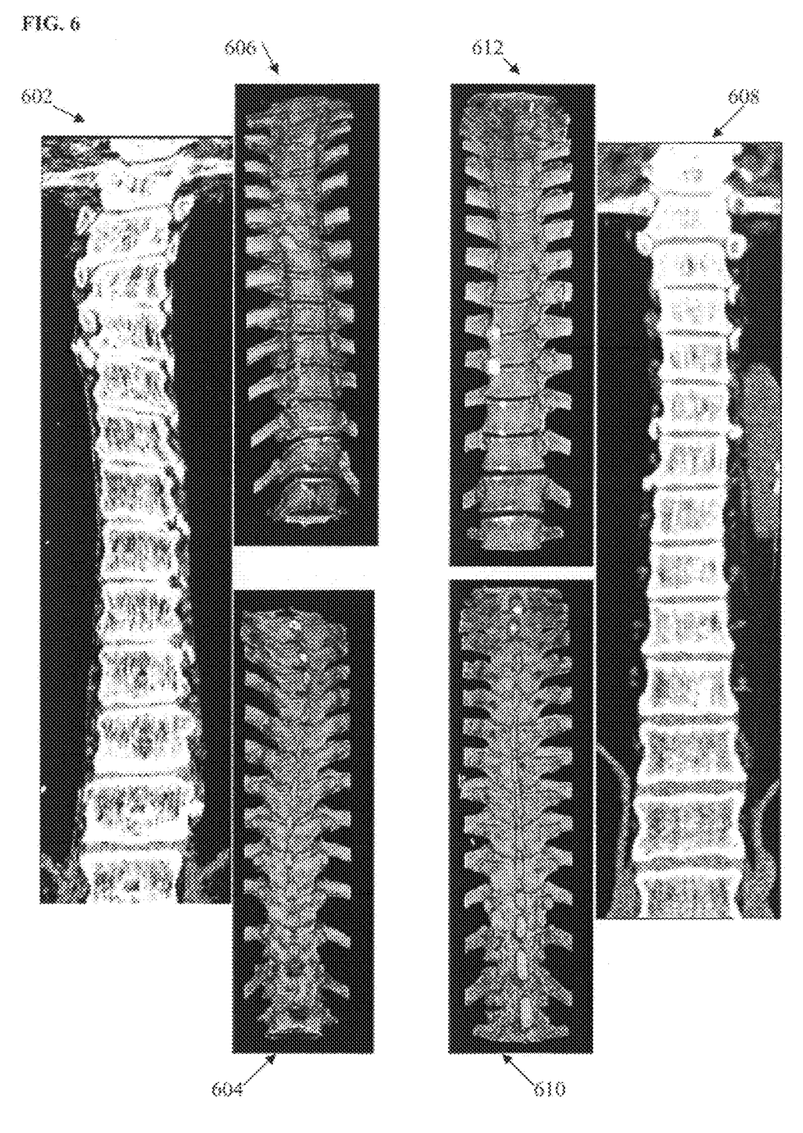
FIG. 6 illustrates exemplary reformatted image volumes generated using the method of FIG. 5.

At step 106, a reformatted image volume is generated based on the spinal cord centerline. According to various embodiments of the present invention, the reformatted image volume can be a straightened volume that allows for easy viewing of the vertebrae (FIGS. 2 and 4), or the reformatted image can be a Multi-planar Reconstruction (MPR) based volume that preserves the curvature of the spine in the coronal plane (FIGS. 5 and 6).

Figure 2:
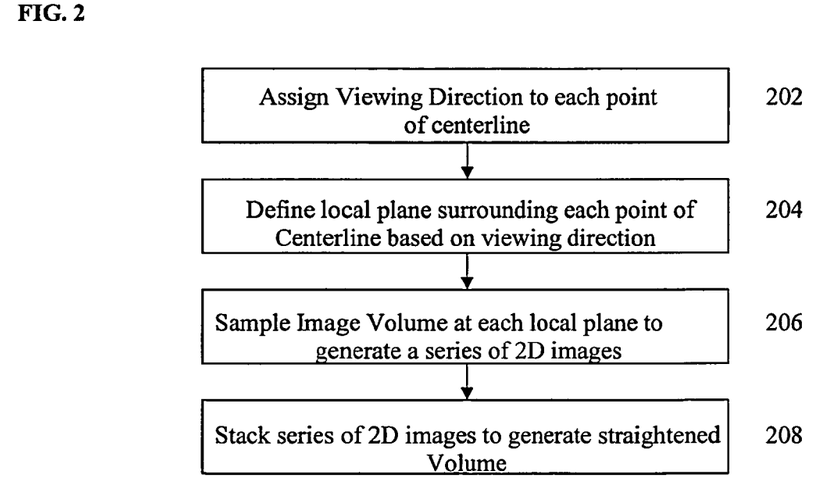
FIG. 2 illustrates a method for generating a reformatted image volume according to an embodiment of the present invention.
Figure 3:
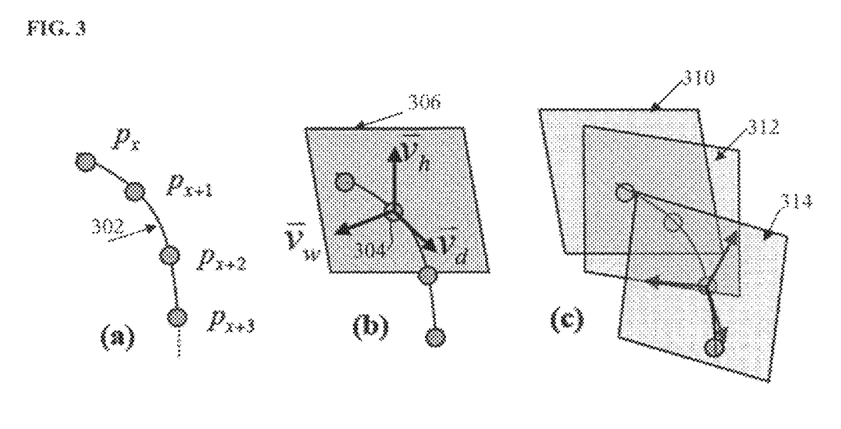
FIG. 3 illustrates generating a portion of a straightened spine volume.

FIG. 2 illustrates a method for generating a reformatted image volume according to an embodiment of the present invention. The method of FIG. 2 can be performed to implement step 106 of FIG. 1, and generate a volume in which the spine is completely straightened. FIG. 3 illustrates the sampling planes used in generating the straightened spine volume, and is referred when describing the method of FIG. 2. At step 202, a viewing direction is assigned to each of the centerline points $P_r \in [p_1 \ldots p_M]$. The viewing directions define a perpendicular plane used for sampling the original data at each centerline point. The viewing direction $\vec{v}_d$ for each point is assigned based on the heading of the next series points; i.e., this vector can point in the direction of its next neighboring point or series of neighboring points. The viewing direction $\vec{v}_d$ determines the normal of the plane that will be sampled. The remaining orthogonal vectors $(\vec{v}_h, \vec{v}_w)$ determine the rotation within the plane. Since these vectors point in the same relative directions as in the original volume, the reformatted volume will have similar directions to the original volume. For example, the left side of the patient in the original volume will correspond to the same approximate direction in the reformatted volume. Spherical linear interpolation can be performed to ensure smooth directional changes between the centerline points. Image (a) of FIG. 3 shows a centerline 302 defined by centerline points $p_x$, $p_{x+1}$, $p_{x+2}$, and $p_{x+3}$. Image (b) of FIG. 3 shows the viewing direction $\vec{v}_d$ determined for centerline point 304. As shown in image (b) of FIG. 3, the viewing direction $\vec{v}_d$ is approximately tangent to the centerline, and the vectors $\vec{v}_h$ and $\vec{v}_w$ are orthogonal to $\vec{v}_d$.

At step 204, a local plane surrounding each centerline point is defined based on the viewing direction of each point. At each point of the centerline, a local plane centered at the centerline point and orthogonal to the viewing direction is defined. Accordingly, the local plane at each point is defined by the vectors $\vec{v}_h$ and $\vec{v}_w$ at that point. The height and width of the local plane are limited to mainly include the vertebra. The height and width can be hardcoded and constant based on expected dimensions of the vertebra, or can be variable based upon segmentation results for a particular patient. It is possible to increase the dimensions of the local plane to include other anatomic objects in addition to the spine. Image (b) of FIG. 3 shows a local plane 306 defined at the centerline point 304.

At step 206, the image volume is sampled at each local plane to generate a series of 2D images. A 2D image is generated at each local plane by sampling the original image volume about the plane. The image data for each point in each local plane is defined based on the image data in the original image volume. The 2D image corresponding to each local plane can be generated by sampling the original image volume using tri-linear interpolation or other well known sampling methods. Image (c) of FIG. 3 shows a series of 2D images 310, 312, and 314 resulting from sampling in local planes.

At step 208, the series of 2D images are stacked together to generate a straightened volume. For example, the 2D images 310, 312, and 314 of image (c) of FIG. 3 can be stacked to for a straightened 3D image volume.

Figure 4:
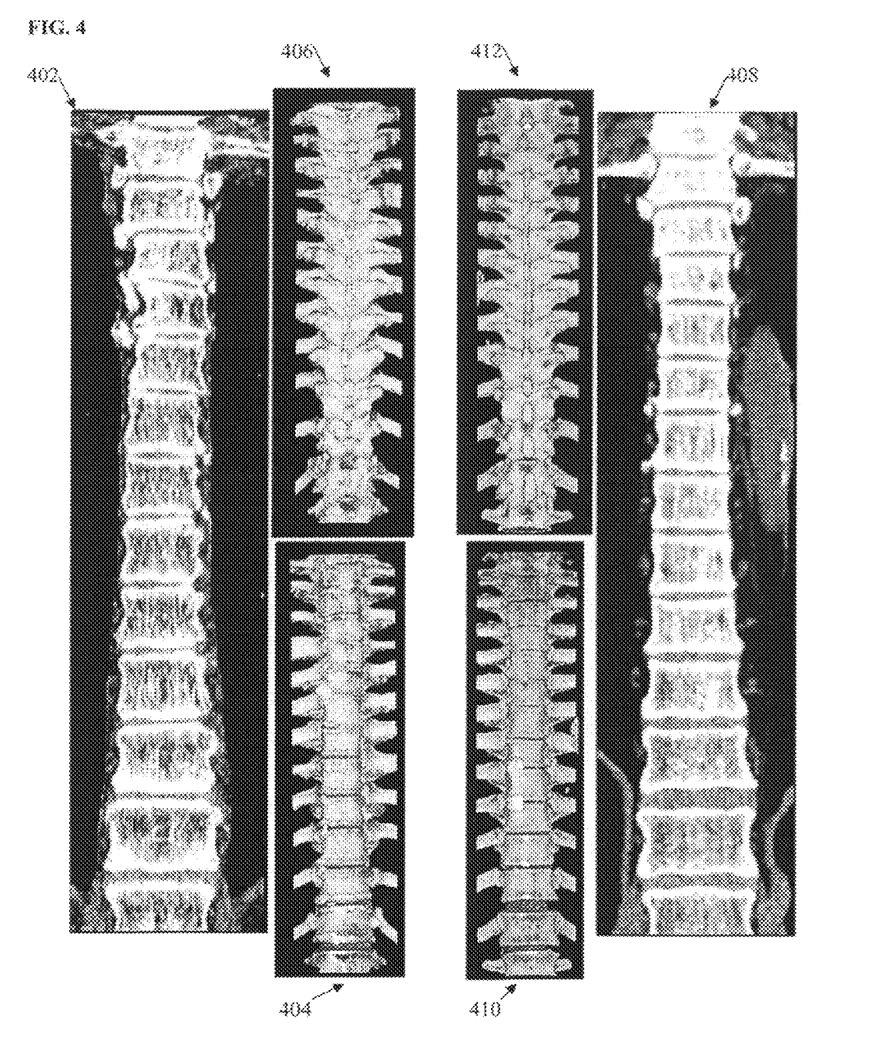
FIG. 4 illustrates exemplary reformatted image volumes generated using the method of FIG. 2.

FIG. 4 illustrates exemplary reformatted CT image volumes generated using the method of FIG. 2. As illustrated in FIG. 4, images 402, 404, and 406 are views of a straightened spine volume of a spine with an abnormal curvature. Image 402 is a coronal slice of the reformatted volume, image 404 is a volume rendering of the reformatted volume from the front, and image 406 is a volume rendering of the reformatted volume from the back. Images 408, 410, and 412 are views of a straightened spine volume of a spine with a relatively normal curvature. Image 408 is a coronal slice of the reformatted volume, image 410 is a volume rendering of the reformatted volume from the front, and image 412 is a volume rendering of the reformatted volume from the back. The individual vertebrae are easy to see and analyze in straightened volumes. However, defects of the spine involving its curvatures, such as scoliosis, may be difficult to detect. Comparing image 402

(abnormal curvature) to image 408 (normal curvature), it can be seen that the straightened images mostly hide the curvature of the spine, although defects are noticeable in the upper and lower vertebrae of image 402.

FIG. 5 illustrates a method for generating a reformatted image volume according to another embodiment of the present invention. The method of FIG. 5 can be performed to implement step 106 of FIG. 1, and generates an MRP based volume that aligns the spine along the natural curvature of the spine. This method reformats the image volume based on a curved MPR automatically defined through the spine centerline. The MRP base volume generated by this method eliminates the curvature of the spine in the posterior to anterior direction, but preserves the curvatures of the spine in the left to right directions. In this method, the viewing directions for the centerline points are not necessary, and the spine is centered within the volume in the automatic generation of the reformatted image volume.

At step 502, the average of the x-coordinates of the centerline points $P_i \in [p_1 \ldots p_M]$ is calculated. As used herein, the x-coordinate and x direction refers to the left and right or horizontal direction of a patient. This average is used to center the final volume sampling region within the center of the vertebra. Similar to the previous method, planar samples are taken from the volume and stack together. The planes are all parallel to the transverse plane and stacked upon each other relative to the offset in the x direction. Offsets in the y directions are ignored.

At step 504, a shift value from the average of the x-coordinates is determined for each centerline point. The shift value for a centerline point is a distance in the x-direction of that centerline point from the average of the x-coordinates of all of the centerline points.

At step 506, a 2D image is sampled at each centerline point resulting in a series of 2D images. Each 2D image is sampled in a local axial plane at each centerline point, i.e., in the transverse plane for all points. The height and width of the local plane are limited to mainly include the vertebra. The height and width can be hardcoded and constant based on expected dimensions of the vertebra, or can be variable based upon segmentation results for a particular patient. It is possible to increase the dimensions of the local plane to include other anatomic objects in addition to the spine. The 2D image at each centerline point can be generated by sampling the original image volume using tri-linear interpolation or other well known sampling methods.

At step 508, the series of 2D images are stacked, with each 2D image shifted in the x-direction from the average of the x-coordinates by the shift value of the corresponding centerline point. Accordingly, the 2D images are aligned in the front-back direction, but 2D each image is shifted in the right-left (x) direction based on the location of the centerline point corresponding to that image. This results in a reformatted image volume in which the curvature of the spine is preserved in the left and right directions.

FIG. 6 illustrates exemplary reformatted CT image volumes generated using the method of FIG. 5. As illustrated in FIG. 6, images 602, 604, and 606 are views of a MPR based reformatted volume of a spine with an abnormal curvature. Image 602 is a coronal slice of the reformatted volume, image 604 is a volume rendering of the reformatted volume from the front, and image 606 is a volume rendering of the reformatted volume from the back. Images 608, 610, and 612 are views of a MPR based reformatted volume of a spine with a relatively normal curvature. Image 608 is a coronal slice of the reformatted volume, image 610 is a volume rendering of the reformatted volume from the front, and image 612 is a volume rendering of the reformatted volume from the back. As illustrated in FIG. 6, curvatures of the spine in the coronal plane (left-right direction) are visible in the MPR based reformatted image volumes. Comparing image 602 (abnormal curvature) to image 608 (normal curvature), the abnormal curvatures in image 602 can be easily seen.

Returning to FIG. 1, at step 108, the reformatted image volume, such as a reformatted image volume generated using the method of FIG. 2 or the method of FIG. 5, is output. The reformatted image volume can be outputted by displaying the reformatted image volume on a display, such as a display of a computer system. As shown in FIGS. 4 and 6, the reformatted image volume can be displayed in 2D slices of the reformatted image volume, as well as 3D volume renderings of the reformatted image volume. The reformatted image volume can also be output by printing images of the reformatted image volume, storing the reformatted image volume on memory or storage of a computer system, and outputting the reformatted image volume and centerline for use in an image processing application, such as a segmentation application, a diagnostic application, or an application for interactive user analysis.

Figure 7:
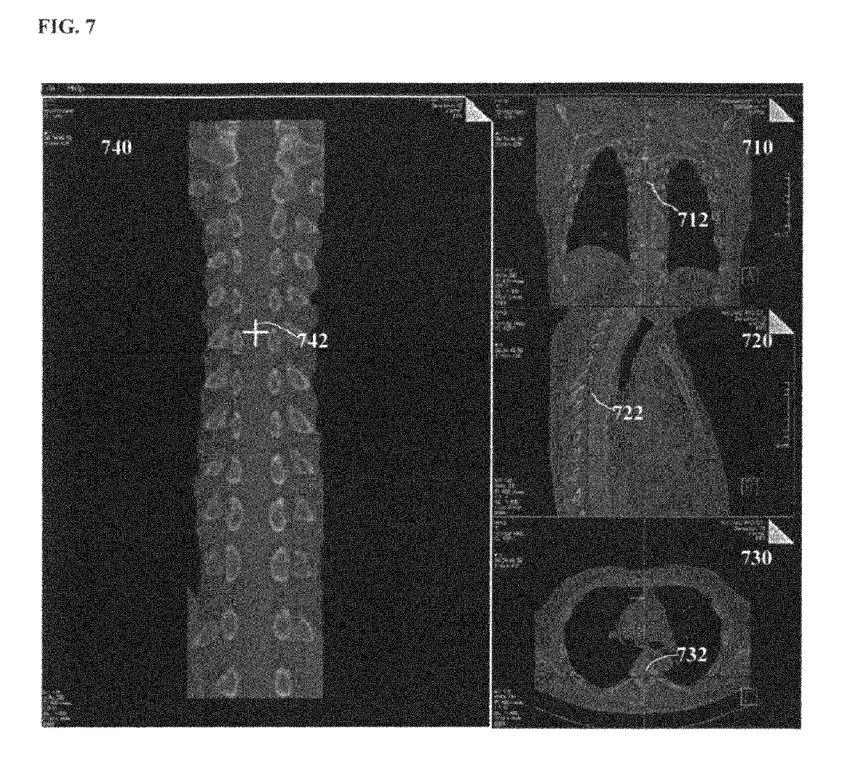
FIG. 7 illustrates displaying a reformatted image volume in a spine analysis application.

FIG. 7 illustrates displaying a reformatted image volume in a computer implemented spine analysis application. The application of FIG. 7 allows for user interaction to analyze the spine using the reformatted image volume. In addition to the original volume, the application is capable of displaying a straightened reformatted image and an MPR base reformatted image. As illustrated in FIG. 7, the application displays coronal, sagittal, and axial slices 710, 720, and 730 of the original image volume. The application also displays a coronal slice 740 of the reformatted image volume. The coronal slice 740 is a slice of a straightened reformatted volume generated as described above in FIG. 2. Since a reformatted volume dataset is generated, the reformatted volume can displayed as slices (such as slice 740), a function of several slices, or 3D volume renderings. The application can map between the reformatted image volume and the original image volume. A user selection point 742 is shown in the coronal slice 740 of the reformatted volume, and corresponding locations 712, 722, and 732 are shown in the coronal, sagittal, and axial slices 710, 720, and 730 of the original image volume. This mapping allows for verification and further analysis of areas of interest. Additionally, the mapping can allow for accurate measurements to be conducted between two given points in the reformatted volume.

Figure 8:
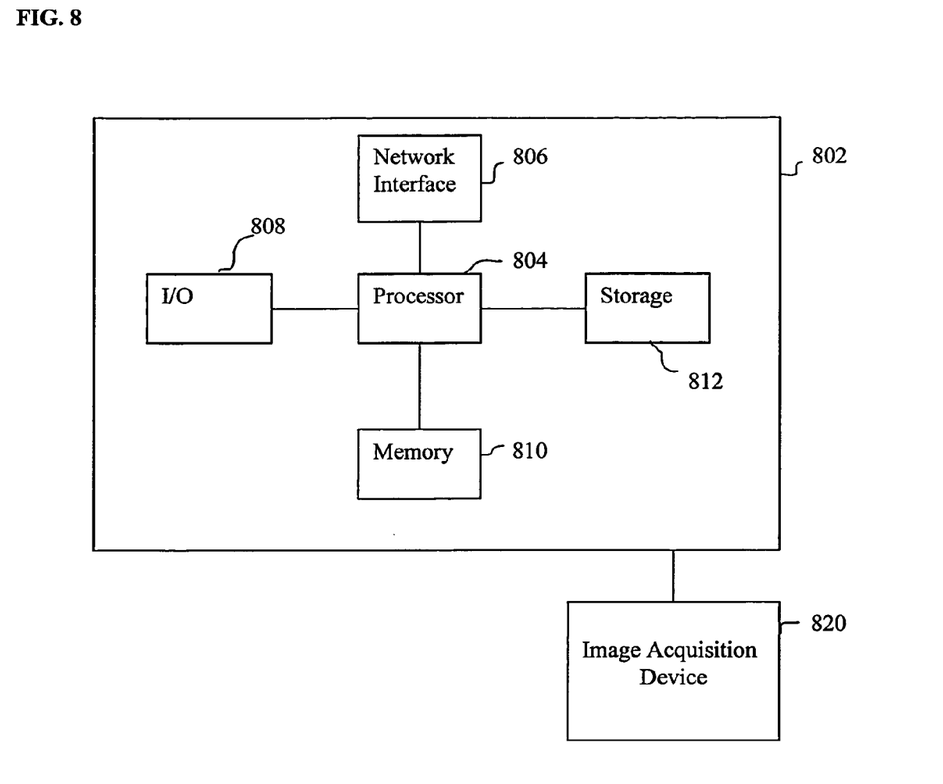
FIG. 8 is a high level block diagram of a computer capable of implementing the present invention.

The above described spine visualization methods can be implemented on a computer using well-known computer processors, memory units, storage devices, computer software, and other components. A high level block diagram of such a computer is illustrated in FIG. 8. Computer 802 contains a processor 804 which controls the overall operation of the computer 802 by executing computer program instructions which define such operation. The computer program instructions may be stored in a storage device 812 (e.g., magnetic disk) and loaded into memory 810 when execution of the computer program instructions is desired. Thus, applications the method steps of the methods of FIGS. 1, 2, and 5, as well as the application shown in FIG. 7 can be defined by the computer program instructions stored in the memory 810 and/or storage 812 and controlled by the processor 804 executing the computer program instructions. Furthermore, the original and reformatted image volume data can be stored in the memory 810 and/or the storage 812. An image acquisition device 820, such as a CT scanning device, can be connected to the computer 802 to input scanned 3D image volumes to the computer 802. It is possible to implement the image acquisition device 820 and the computer 802 as one device. It is also possible the image acquisition device 820 and the computer 802 communicate wirelessly through a network. The computer 802 also includes one or more network interfaces 806 for communicating with other devices via a network. The computer 802 also includes other input/output devices 808 that enable user interaction with the computer 802 (e.g., display, keyboard, mouse, speakers, buttons, etc.) One skilled in the art will recognize that an implementation of an actual computer could contain other components as well, and that FIG. 8 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for spine visualization in a 3D image volume comprising:
   receiving an input 3D image volume;
   determining a spinal cord centerline in said input 3D image volume using a fully automatic spinal cord tracing based method that fits an annulus model having an inner radius and an outer radius to high contrast portions in spinal canal regions of slices of the 3D image volume based on a contrast score calculated using a difference between average image data between the inner radius and the outer radius and average image inside the inner radius, and smoothes a trajectory of said spinal cord centerline; and
   generating a reformatted image volume from said input 3D image volume based on said spinal cord centerline.

2. The method of claim 1, further comprising:
   displaying the reformatted image volume.

3. The method of claim 2, wherein said step of displaying the reformatted image volume comprises displaying at least one of a 2D slice of the reformatted image volume and a 3D volume rendering of the reformatted image volume.

4. The method of claim 1, wherein said step of determining a spinal cord centerline comprises:
   determining a series of points in said input 3D image volume, each point representing a spinal cord position in an axial slice of said input 3D image volume; and
   interpolating the series of points to generate a set of equidistant points defining said spinal cord centerline.

5. The method of claim 1, wherein said step of generating a reformatted image volume from said input 3D image volume based on said spinal cord centerline comprises generating at least one of a straightened spine reformatted image volume and a Multi-planar Reconstruction (MPR) based reformatted image volume based on said spinal cord centerline.

6. The method of claim 1, wherein said spinal cord centerline comprises a set of centerline points defining said spinal cord centerline and said step of generating a reformatted image volume from said input 3D image volume based on said spinal cord centerline comprises:
   assigning a viewing direction to each centerline point;
   defining local planes at the centerline points, each local plane centered at a centerline point and orthogonal to the viewing direction assigned to the centerline point;
   sampling said 3D image volume at each local plane to generate a series of 2D images; and
   stacking the series of 2D images such that the 2D images are aligned to generate a straightened reformatted image volume.

7. The method of claim 6, wherein each of the local planes has a predetermined height and a predetermined width, such that only image data surrounding the vertebrae in said 3D image volume is sampled during said sampling step.

8. The method of claim 1, wherein said spinal cord centerline comprises a set of centerline points defining said spinal cord centerline and said step of generating a reformatted image volume from said input 3D image volume based on said spinal cord centerline comprises:
   calculating an average of x-coordinates of the centerline points, wherein the x-coordinate of a centerline point is a position of the centerline point in a right-left direction of a patient's body in said input 3D image volume;
   determining a shift value from said average of x-coordinates for each centerline point;
   sampling said 3D image volume at local planes centered at each centerline point and orthogonal to a vertical direction of the patient's body in said input 3D image volume to generate a series of 2D images, each 2D image corresponding to a centerline point; and
   stacking the series of 2D images such the 2D images are aligned in a front-back direction of the patient's body in said input 3D image volume and each 2D image is shifted in the right-left direction by the shift value determined for the corresponding centerline point.

9. An apparatus for spine visualization in a 3D image volume comprising:
   a processor; and
   a non-transitory memory to store computer program instructions, the computer program instructions when executed by the processor causing the processor to perform operations comprising:
   receiving an input 3D image volume;
   determining a spinal cord centerline in said input 3D image volume using a fully automatic spinal cord tracing based method that fits an annulus model having an inner radius and an outer radius to high contrast portions in spinal canal regions of slices of the 3D image volume based on a contrast score calculated using a difference between average image data between the inner radius and the outer radius and average image inside the inner radius, and smoothes a trajectory of said spinal cord centerline; and
   generating a reformatted image volume from said input 3D image volume based on said spinal cord centerline.

10. The apparatus of claim 9, wherein the operations further comprise:
    displaying the reformatted image volume.

11. The apparatus of claim 9, wherein said determining a spinal cord centerline comprises:
    determining a series of points in said input 3D image volume, each point representing a spinal cord position in an axial slice of said input 3D image volume; and
    interpolating the series of points to generate a set of equidistant points defining said spinal cord centerline.

12. The apparatus of claim 9, wherein generating a reformatted image volume from said input 3D image volume based on said spinal cord centerline comprises:

generating at least one of a straightened spine reformatted image volume or a Multi-planar Reconstruction (MPR) based reformatted image volume based on said spinal cord centerline.

13. The apparatus of claim 9, wherein said spinal cord centerline comprises a set of centerline points defining said spinal cord centerline and generating a reformatted image volume from said input 3D image volume based on said spinal cord centerline comprises:
 assigning a viewing direction to each centerline point;
 defining local planes at the centerline points, each local plane centered at a centerline point and orthogonal to the viewing direction assigned to the centerline point;
 sampling said 3D image volume at each local plane to generate a series of 2D images; and
 stacking the series of 2D images such that the 2D images are aligned to generate a straightened reformatted image volume.

14. The apparatus of claim 13, wherein each of the local planes has a predetermined height and a predetermined width, such that only image data surrounding the vertebrae in said 3D image volume is sampled during said sampling step.

15. The apparatus of claim 9, wherein said spinal cord centerline comprises a set of centerline points defining said spinal cord centerline and generating a reformatted image volume from said input 3D image volume based on said spinal cord centerline comprises:
 calculating an average of x-coordinates of the centerline points, wherein the x-coordinate of a centerline point is a position of the centerline point in a right-left direction of a patient's body in said input 3D image volume;
 determining a shift value from said average of x-coordinates for each centerline point;
 sampling said 3D image volume at local planes centered at each centerline point and orthogonal to a vertical direction of the patient's body in said input 3D image volume to generate a series of 2D images, each 2D image corresponding to a centerline point; and
 stacking the series of 2D images such the 2D images are aligned in a front-back direction of the patient's body in said input 3D image volume and each 2D image is shifted in the right-left direction by the shift value determined for the corresponding centerline point.

16. A non-transitory computer readable medium encoded with computer executable instructions for spine visualization in a 3D image volume, the computer executable instructions defining steps comprising:
 receiving an input 3D image volume;
 determining a spinal cord centerline in said input 3D image volume using a fully automatic spinal cord tracing based method; and
 generating a reformatted image volume from said input 3D image volume based on said spinal cord centerline.

17. The non-transitory computer readable medium of claim 16, further comprising computer executable instructions defining the step of:
 displaying the reformatted image volume.

18. The non-transitory computer readable medium of claim 17, wherein the computer executable instructions defining the step of displaying the reformatted image volume comprise computer executable instructions defining the step of:
 displaying at least one of a 2D slice of the reformatted image volume and a 3D volume rendering of the reformatted image volume.

19. The non-transitory computer readable medium of claim 16, wherein the computer executable instructions defining the step of determining a spinal cord centerline comprise computer executable instructions defining the steps of:
 determining a series of points in said input 3D image volume, each point representing a spinal cord position in an axial slice of said input 3D image volume; and
 interpolating the series of points to generate a set of equidistant points defining said spinal cord centerline.

20. The non-transitory computer readable medium of claim 16, wherein the computer executable instructions defining the step of generating a reformatted image volume from said input 3D image volume based on said spinal cord centerline comprise computer executable instructions defining the step of:
 generating at least one of a straightened spine reformatted image volume and a Multi-planar Reconstruction (MPR) based reformatted image volume based on said spinal cord centerline.

21. The non-transitory computer readable medium of claim 16, wherein said spinal cord centerline comprises a set of centerline points defining said spinal cord centerline and the computer executable instructions defining the step of generating a reformatted image volume from said input 3D image volume based on said spinal cord centerline comprise computer executable instructions defining the steps of:
 assigning a viewing direction to each centerline point;
 defining local planes at the centerline points, each local plane centered at a centerline point and orthogonal to the viewing direction assigned to the centerline point;
 sampling said 3D image volume at each local plane to generate a series of 2D images; and
 stacking the series of 2D images such that the 2D images are aligned to generate a straightened reformatted image volume.

22. The non-transitory computer readable medium of claim 21, wherein each of the local planes has a predetermined height and a predetermined width, such that only image data surrounding the vertebrae in said 3D image volume is sampled during said sampling step.

23. The non-transitory computer readable medium of claim 16, wherein said spinal cord centerline comprises a set of centerline points defining said spinal cord centerline and the computer executable instructions defining the step of generating a reformatted image volume from said input 3D image volume based on said spinal cord centerline comprise computer executable instructions defining the steps of:
 calculating an average of x-coordinates of the centerline points, wherein the x-coordinate of a centerline point is a position of the centerline point in a right-left direction of a patient's body in said input 3D image volume;
 determining a shift value from said average of x-coordinates for each centerline point;
 sampling said 3D image volume at local planes centered at each centerline point and orthogonal to a vertical direction of the patient's body in said input 3D image volume to generate a series of 2D images, each 2D image corresponding to a centerline point; and
 stacking the series of 2D images such the 2D images are aligned in a front-back direction of the patient's body in said input 3D image volume and each 2D image is shifted in the right-left direction by the shift value determined for the corresponding centerline point.

* * * * *